US011096827B1

(12) United States Patent
Kono et al.

(10) Patent No.: US 11,096,827 B1
(45) Date of Patent: Aug. 24, 2021

(54) PPE INTEGRATIVE PROTECTIVE EYEWEAR

(71) Applicants: Alvin Kono, Honolulu, HI (US); Collin Kobayashi, Honolulu, HI (US)

(72) Inventors: Alvin Kono, Honolulu, HI (US); Collin Kobayashi, Honolulu, HI (US)

(*) Notice: Subject to any disclaimer, the term of this patent is extended or adjusted under 35 U.S.C. 154(b) by 0 days.

(21) Appl. No.: 17/163,027

(22) Filed: Jan. 29, 2021

Related U.S. Application Data

(60) Provisional application No. 63/054,607, filed on Jul. 21, 2020.

(51) Int. Cl.
| *A61F 9/02* | (2006.01) |
| *A41D 13/11* | (2006.01) |
| *G02C 11/04* | (2006.01) |
| *G02C 5/00* | (2006.01) |
| *A62B 18/02* | (2006.01) |

(52) U.S. Cl.
CPC .......... *A61F 9/028* (2013.01); *A41D 13/1184* (2013.01); *A61F 9/029* (2013.01); *A62B 18/02* (2013.01); *G02C 5/008* (2013.01); *G02C 11/04* (2013.01)

(58) Field of Classification Search
CPC ... A41D 13/1184; A62B 18/02; A63B 33/002; G02C 5/008; G02C 11/04; A61F 9/025; A61F 9/028; A61F 9/029
USPC .......................................................... 2/428
See application file for complete search history.

(56) References Cited

U.S. PATENT DOCUMENTS

| 1,433,676 | A | | 10/1922 | Cover |
| 1,720,814 | A | | 7/1929 | Baker |
| 2,291,603 | A | | 8/1942 | Barker |
| 2,636,171 | A | | 4/1953 | Aspenleiter |
| 2,649,395 | A | * | 8/1953 | Maurer ................... A61F 9/029 156/253 |
| 2,654,090 | A | | 10/1953 | Christensen |
| 2,877,463 | A | | 3/1959 | Watkins |

(Continued)

FOREIGN PATENT DOCUMENTS

| CN | 111358620 A | 7/2020 |
| CN | 211832938 U | 11/2020 |

(Continued)

OTHER PUBLICATIONS

Johns Hopkins Bloomberg School of Public Health, The Right Mask for the Task, accessed online on May 2, 2020 @ https://www.jhsph.edu/covid-19/articles/the-right-mask-for-the-task.html.

(Continued)

*Primary Examiner* — Katherine M Moran
(74) *Attorney, Agent, or Firm* — Watanabe Ing, LLP; Seth M. Reiss (57) ABSTRACT

In one aspect, the invention provides protective eyewear comprising at least one removable filter assembly allowing ambient air to circulate to the eye while filtering out pathogens and other particles. In another aspect, the protective eyewear is adapted to removably receive and secure multiple PPE accessories, including for example face shields and face masks. Together with the protective eyewear, the PPE accessories are fastened to the user through a single head strap. The eyewear can accommodate normal or prescription lenses and is configured with a rigid frame and flexible seal to provide a snug, airtight fit.

16 Claims, 6 Drawing Sheets

(56) References Cited

U.S. PATENT DOCUMENTS

| | | | |
|---|---|---|---|
| 3,141,172 | A | 7/1964 | Hirschmann |
| 3,181,531 | A | 5/1965 | Angioletti |
| 3,298,031 | A * | 1/1967 | Morgan ............. A41D 13/1184 2/9 |
| 3,638,240 | A | 2/1972 | Militello |
| 4,264,988 | A | 5/1981 | Specht |
| 4,689,838 | A | 9/1987 | Angermann et al. |
| 4,785,481 | A | 11/1988 | Palmer |
| 4,977,627 | A | 12/1990 | Metcalfe et al. |
| 5,363,512 | A | 11/1994 | Grabos et al. |
| 5,652,965 | A | 8/1997 | Crooks |
| 5,657,106 | A | 8/1997 | Herald et al. |
| 5,813,398 | A | 9/1998 | Baird et al. |
| 6,049,917 | A | 4/2000 | Ryden |
| 6,138,285 | A | 10/2000 | Robrahn et al. |
| 6,550,914 | B1 | 4/2003 | Kopfer |
| 6,692,124 | B2 | 2/2004 | Katz et al. |
| 6,704,944 | B2 | 3/2004 | Kawainshi et al. |
| 6,718,981 | B2 | 4/2004 | Cardarelli |
| 6,732,382 | B2 | 5/2004 | Dondero |
| 6,763,835 | B1 | 7/2004 | Grove et al. |
| 6,772,448 | B1 | 8/2004 | Hockaday et al. |
| 6,789,273 | B2 | 9/2004 | Markovitz |
| 6,793,336 | B2 | 9/2004 | Min |
| 6,991,333 | B2 | 1/2006 | Van Atta et al. |
| 6,994,433 | B2 * | 2/2006 | Hockaday ............... A61F 9/028 351/62 |
| 7,073,208 | B2 | 7/2006 | Penque et al. |
| 7,488,068 | B2 | 2/2009 | Welchel et al. |
| 7,686,018 | B2 | 3/2010 | Cerbini |
| 7,743,432 | B2 | 6/2010 | Curei |
| 8,402,966 | B2 | 3/2013 | Morgan et al. |
| 8,726,412 | B2 | 5/2014 | Wright |
| 10,098,787 | B2 | 10/2018 | Umentum et al. |
| 10,525,292 | B2 | 1/2020 | Tang et al. |
| 10,556,136 | B2 | 2/2020 | Seppaia |
| 2005/0132478 | A1 * | 6/2005 | Canavan ................ A61F 9/027 2/448 |
| 2006/0055878 | A1 * | 3/2006 | Yee ........................ A61F 9/022 351/159.02 |
| 2008/0086795 | A1 * | 4/2008 | Cyr .................... A41D 13/1184 2/425 |
| 2015/0245675 | A1 * | 9/2015 | Chinquee ................ A61F 9/029 2/424 |
| 2018/0125715 | A1 * | 5/2018 | Bellussi ................. G02C 7/088 |
| 2018/0360662 | A1 * | 12/2018 | Seo ........................ A61F 9/022 |

FOREIGN PATENT DOCUMENTS

| | | |
|---|---|---|
| DE | 0625344 A2 | 11/1994 |
| DE | 102005062370 B4 | 4/2008 |
| GB | 2296854 A | 7/1996 |
| JP | 201046389 A | 3/2010 |
| WO | 2013/075166 A1 | 5/2013 |
| WO | 2019/009589 A1 | 1/2019 |
| WO | 2020/083010 A1 | 4/2020 |

OTHER PUBLICATIONS

New England Journal of Medicine, Aerosol and Surface Stability of SARS-COV-2 compared with SARS-COV-1., Aerosol and Surface Stability of SARS-COV-2 compared with SARS-COV-1, accessed online on May 2, 2020 @ https://www.nejm.org/doi/10.1056/NEJMc2004973.

CDC Centers for Disease Control and Prevention, The National Institute for Occupational Safety and Health (NIOSH), Influenza (flu) in the Workplace. NIOSH activities; Influenza Transmission Research, Mar. 28, 2018, accessed online on May 2, 2020 @ https://www.cdc.gov/niosh/topics/flu/transmission.html.

CDC Centers for Disease Control and Prevention, The National Institute for Occupational Safety and Health (NIOSH), Eye Safety. Workplace Safety & Health topics, accessed on online on May 2, 2020 @ https://www.cdc.gov/niosh/topics/eye/eye-infectious.html.

ISEA International Safety Equipment Association. FEMA guidelines for critical PPE, specifically eye and face protection, amid COVID-10 pandemic. accessed online May 2, 2020 @ https://safetyequipment.org/fema-guidelines-for-critical-ppe/.

George W. Mertz, Considerations in Contact Lens Use under Adverse Conditions: Proceedings of a Symposium. accessed online May 28, 2020 @ https://www.ncbi.nlm.nih.gov/books/NBK234101/.

Carla J. Siegfried, et al. Oxygen Distribution in the Human Eye: Relevance to the Etiology of Open-Angle Glaucoma after Vitrectomy, Nov. 2010, accessed online May 28, 2020, https://www.ncbi.nlm.nih.gov/pmc/articles/PMC3061509/.

* cited by examiner

PPE INTEGRATIVE PROTECTIVE EYEWEAR

CROSS-REFERENCE TO RELATED APPLICATIONS

This patent application claims the benefit of U.S. Provisional Patent Application No. 63/054,607, filed Jul. 21, 2020, by the present inventors, the entire contents of which are incorporated herein in their entirety.

TECHNICAL FIELD OF THE INVENTION

The invention relates generally to protective eyewear and more specifically to a protective eyewear that allows indirect ventilation of eyes while filtering out pathogens and droplets through a removable filter assembly.

BACKGROUND

General eye safety is achieved through the use of safety glasses. These are typically open eyewear protection that leads to an open source of exposure with airborne pathogens. For example, droplet infections through the cornea occur when aerosols and aerosol droplets containing contaminants come in contact with the cornea. Existing safety glasses are not particularly air tight and allow for passage of unventilated air through to the eyes that may then lead to possible infection. Further, the safety glasses are not conducive to be worn over existing prescription glasses.

Closed eyewear protection is also known in the art. However, closed eyewear protection provides total sealing that does not allow for any passage of air. When worn for prolonged periods of time, closed eyewear protection results in fogging of the glasses. Further, corneas do not have blood vessels and require ambient oxygen, the absence of which may result in tissue damage. This is a condition that may be caused by the prolonged use of closed eyewear.

Also, personal protection equipment (PPE) devices are for the most part designed and test fitted independently from each manufacturer. However, in a real-world scenario, multiple devices may be needed for a specific task but may not work together due to fitment issues from head gear crossovers or other crossovers. This limits the selection of use of PPE when combining safety equipment and/or devices or causes discomfort with use, in particular, long duration use.

Thus, there is a need in the art for eyewear protection that protects eyes from airborne pathogens while maintaining air/oxygen flow to the cornea. Further, there is a need for eyewear protection that integrates with other PPEs, including, for example, face masks and face shields, to provide synergistic protection while maintaining practicality and comfort.

BRIEF DESCRIPTION OF THE INVENTION

In one aspect, the subject invention provides a protective eyewear that can filter air to remove particles of a size as determined by the pore size of the filters such that the cornea can still receive oxygen while being protected from pathogens, including viruses and bacteria, and/or particulate matter. Further, the protective eyewear of the invention comprises a filter assembly that is removably attached to a frame of the protective eyewear. This allows for removal of the filter for cleaning, sterilization or replacement.

In a further aspect, the protective eyewear of the invention includes an accessory receiving extension that allows for other PPEs or accessories to be attached to and integrate with the protective eyewear to enhance protection or comfort according to the requirements.

In another aspect, the invention provides a lower frame shaped to accommodate a face mask worn concurrently with the protective eyewear.

In yet another aspect, the invention provides a face shield that is capable of being detachably attached to the protective eyewear of the invention.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

Unless otherwise indicated, all numbers expressing feature sizes, amounts, and physical properties used in the specifications and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the term "or" is generally employed in its sense including "and/or" unless the content clearly dictates otherwise.

Figure 1:
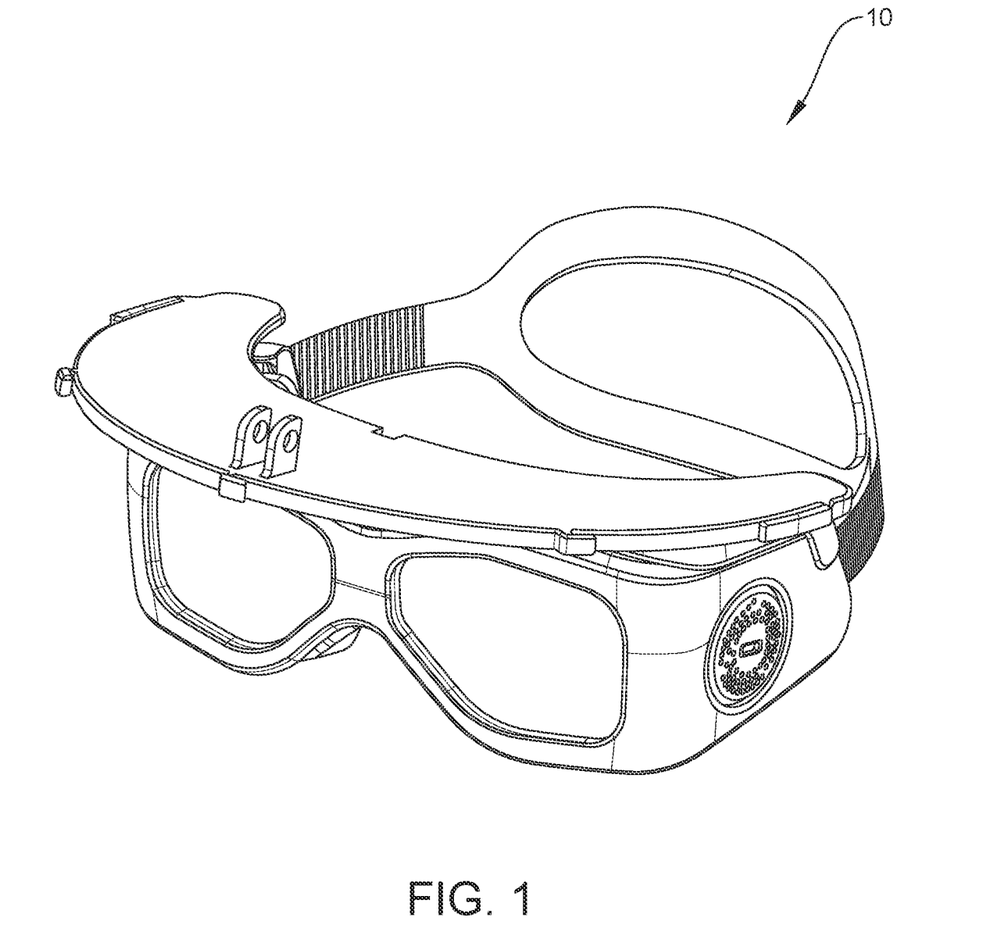
FIG. 1 shows in perspective view a protective eyewear of the subject invention.
Figure 2:
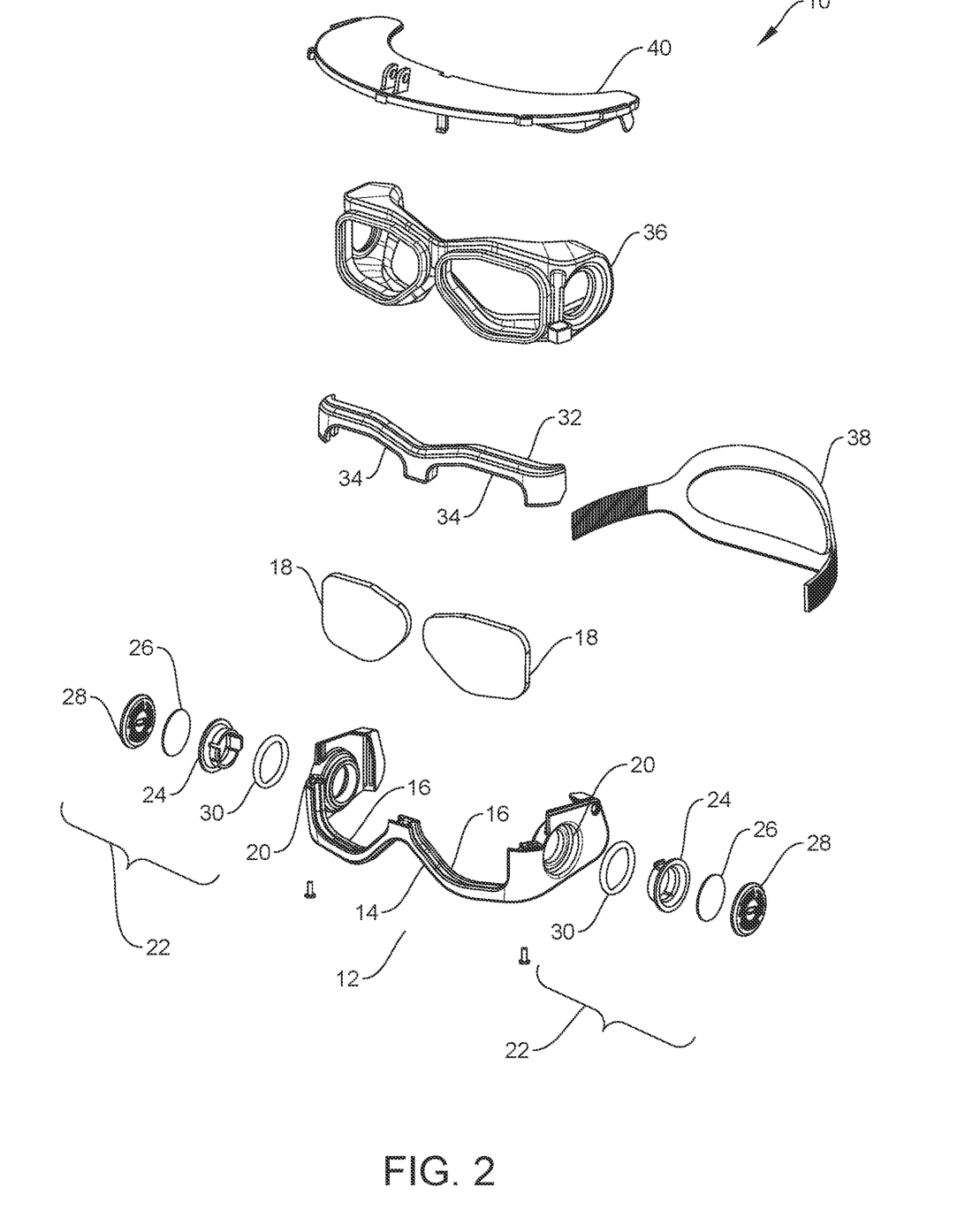
FIG. 2 is an exploded view of the protective eyewear of the invention illustrated in FIG. 1.

As noted herein, in one aspect, the invention provides a protective eyewear. Turning to the drawings, FIG. 1 shows the protective eyewear of the invention, generally depicted by the numeral 10. FIG. 2 shows the protective eyewear of the invention 10 in exploded view. The lower frame 12 has a bottom portion 14 and side portions 16. According to an exemplary embodiment, the bottom portion 14 is made of a rigid material such as polycarbonate, more specifically a polycarbonate that passes impact testing, for example the ANSI Z87.1-2015 impact rating test or the MIL-PRF 32432 Ballistic Fragmentation standard test. Bottom portion 14 comprises slits 16 along its top aspect. The slit has a width sufficient to receive face seal 36 (described below) which, in turn, receives spectacle lens 18.

Since face seal 36 integrates with the upper and lower frame to provide a seal for the user's face. Face seal 36 is made of a flexible material and has slits that receive lenses 18. Once the lens 18 is inserted into the slit, the slit will form an air tight seal around the lens. One particularly useful material for face seal 36 is silicone as it imparts the capability to stretch over the plano lens, and further allows the lens to be upgraded to prescription lens, while still maintaining an air tight seal. Consequently, the protective eyewear of the invention can be used with a non-prescription and prescription lens manufactured by any known technology, such as. for example, step edge process.

The ability to integrate prescription lens into the protective eyewear allows the user to eliminate the eye glass or contact lens which reduces contamination risks noted herein. Thus, the protective eyewear of the invention enables its use along with other accessories while still maintaining protection from airborne contamination and maintaining airflow to the cornea.

The side portions 16 of frame 12 comprise a filter assembly receptacle 20 comprising attachment means through which the filter assembly 22 can be removably attached. Typical attachment means useful in the invention include a snap fit lock mechanism. Filter assembly 22 comprises a filter housing 24 that is capable of being received through the attachment means of the filter assembly receptacle 20. According to the exemplary embodiment depicted, the filter assembly 22 further includes a filter 26, a filter cover 28 and an O-ring 30.

Typical filter materials useful in the invention include, but are not limited to a composite filter media of a plurality of layers. The central layer of electrostatically charged material may be formed with a mixture of polyolefin fibers such as polypropylene and electro-negative substituted organic resin fibers such as modacrylic acrylonitrile-vinyl to efficiently filter more than 99% of 0.1 micron particles. A prefilter layer such as polyester removes large particles, creates tear resistance, and may also impart flame retardancy. It will be obvious to one skilled in the art that the choice of the filter materials ensure that no pathogen will be able to penetrate the barrier whereas gases such as oxygen can go through to the cornea. Since the filter assembly is removably attached to the side portions of the bottom frame of the protective eyewear, the filter can be removed for cleaning on a regular basis or for periodical replacement. The filter cover 28 holds the filter 26 in place by any known means that ensures air tight coverage and compression, for example, by sonic welding the two components together.

While filter assembly receptacle 20 is shown in FIG. 2 as located one on either side of frame 12, embodiments in which just one filter assembly receptacle, or more than two filter assembly receptacles, and in which the receptacles 20 are located on frame 12 other than along each side, are also envisioned.

Frame 12 can be made of a hard plastic material such as acrylics, which provides appropriate rigidity to the protective eyewear. The choice of material also allows it to be manufactured in various colors as required. Further, images such as brand names and logos can be included in the frame as necessary. The side portions may also be molded to the bottom portion. Alternately, the side portions may be removably attached to the bottom portion through suitable attachment means.

The filter assembly receptacle has a secure method, such as a screw on lid that creates a pressure to clamp and to secure the filter assembly that holds the filter in place. The filter is generally defined by its pore size, which in turn will determine the size of particles that can pass through it. In some embodiments, the filter is chosen such that it has the capability to block down to pathogen size. In case of the screw method, variables such as threaded or fraction of a turn fastener can be utilized. The fraction of turn allows a pin on the lid to turn and ride up a ramp on the compartment into a divot which secures the position, creating tension and a holding mechanism. The surface cover of the filter assembly lid can allow a gap as all air will bypass the filter compartment. The filter assembly has a binding mechanism from two surfaces that holds and secures the filter in place when the lid is secured into place.

Figure 3A:
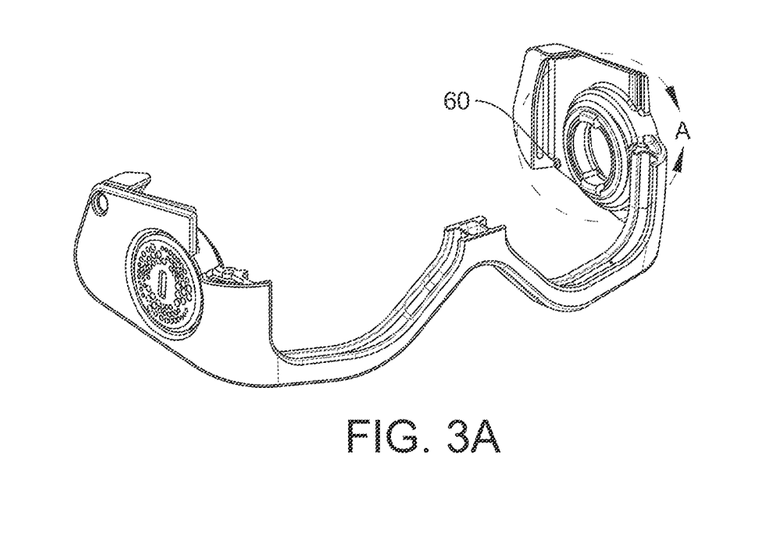
FIG. 3A is a perspective view of the lower frame of the protective eyewear showing the filter assembly and the filter assembly receptacle on the side portion of the lower frame.
Figure 3B:
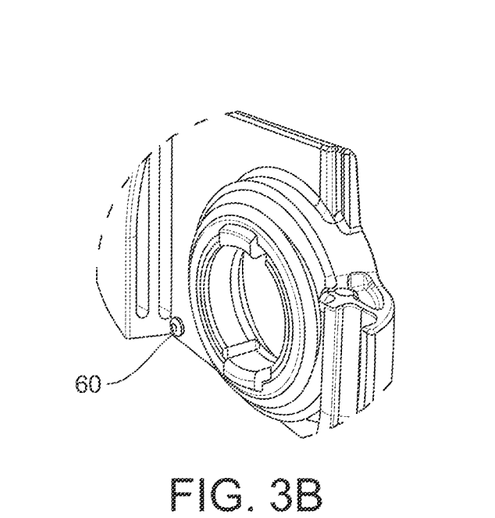
FIG. 3B is an enlarged view of the filter assembly receptacle within the lower frame, showing the details thereof including a face mask receiving knob extending from the lower frame.

FIG. 3A shows one exemplary embodiment of the attachment means of the filter assembly to the side portion of the lower frame. In this embodiment, a snap in clip design to hold filter to frame is shown. FIG. 3B illustrates the filter assembly having the complementary snap in clip design shown in FIG. 3A in further detail.

Figure 3C:
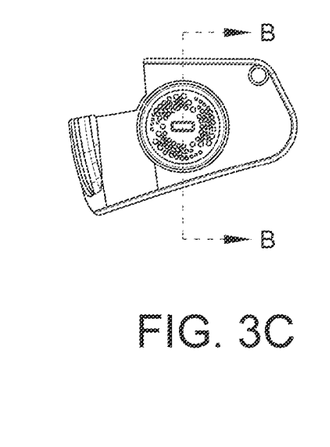
FIG. 3C shows details of the filter assembly secured within the protective eyewear lower frame.
Figures 3D, 3E, 3F:
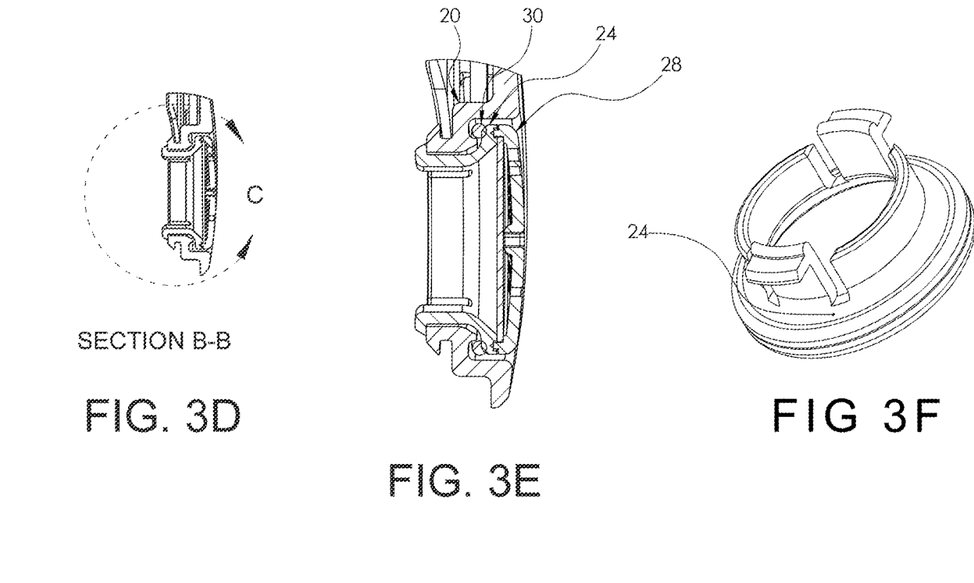
FIG. 3D is a cross-section taken along line B-B of FIG. 3C showing the filter assembly secured within the frame.
FIG. 3E is an enlarged drawing of the cross-section shown in FIG. 3D illustrating the detail thereof.
FIG. 3F illustrates in perspective view the filter assembly housing with snap-in clip mechanism.

FIGS. 3C, 3D, 3E and 3F further illustrate the details of the filter assembly secured by the filter assembly receptacle that is built into the lower frame. FIG. 3D is a cross section taken along lines B-B of FIG. 3C, showing the filter assembly receptacle securing the filter assembly within the frame. FIG. 3E shows the details of the filter assembly of FIG. 3D in enlarged format. The snap-fit lock extending from the bottom of the filter assembly is shown in FIG. 3F.

Referring to FIG. 3E, filter assembly 22 comprises filter housing 24 and housing cover 28. Housing 24 is inserted into filter assembly receptacle 20 with seal 30 positioned between housing 24 and receptacle 20 to form an airtight lock. This air tight lock is achieved through the use of O-ring seal 30, and the snap-clip or lock mechanism that extends from the bottom.

In some embodiments, the filter assembly can be used without a filter in place. In that case, the filter assembly comprises only the housing, filter cover and the O-ring.

Thus, the filter assembly still provides protection depending on other protective equipment in use as described herein.

The filter assembly is configured such that it integrates into the frame and provides an indirect path from ventilation to eye space. The indirect path allows environment air to enter an open vent in the frame, the air then passes the filter assembly which includes the filter, which then filters the air that enters the eye chamber. This allows the filtered air to the reach the cornea of the eye which relies on environmental air for oxygen distribution.

In some embodiments, the invention includes a face mask and comprises a face mask attachment means that allows for the face mask to be secured in position to the protective eyewear of the invention. In FIGS. 3A and 3B, one embodiment of the face mask attachment means is shown depicted by numeral 60. Here, a knob 60 is provided such that one or more loops extending from the face mask loop over the face mask attachment means 60 in order to secure it firmly in place. Other such variations of the attachment means such as interlocking fibers and the like would become apparent to one skilled in the art and is contemplated to be within the scope of the invention Returning to FIG. 2, the protective eyewear 10 further comprises an upper frame 32. The bottom aspect of the upper frame 32 comprises a pair of slits 34 that receive face seal 36 which, in turn has slits to receive the pair of lens 18. The upper portion of face seal 36 is made of a similarly flexible material as the bottom portion that enables it to sealably receive the lens 18.

In one embodiment, the side portions comprising the filter assembly receptacles may be fitted to the upper frame of the protective eyewear instead of the lower frame. In another embodiment, the side portions are divided into two halves, each half attached to the lower and upper frame respectively, and they can be attached to each other through suitable attachment means.

Figure 4A:
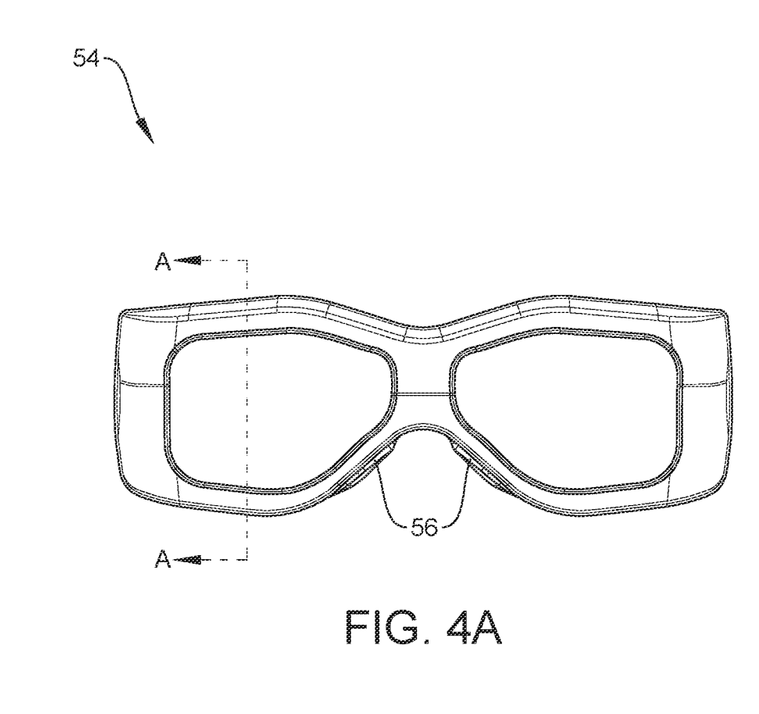
FIG. 4A is a front view of the face seal used in the protective eyewear of the invention.
Figure 4B:
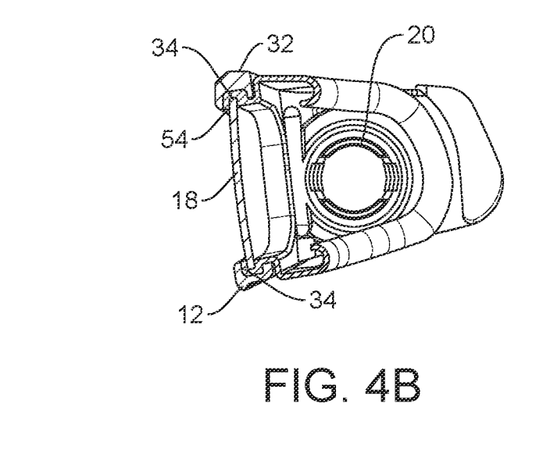
FIG. 4B is a cross-section taken along line A-A of FIG. 4A showing the face seal securing a lens within the frame of the protective eyewear of the invention.
Figure 5A:
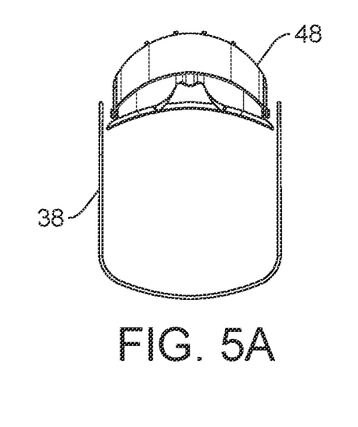
FIG. 5A is a bottom view of a face shield removably affixed to the protective eyewear of the invention.
Figure 5B:
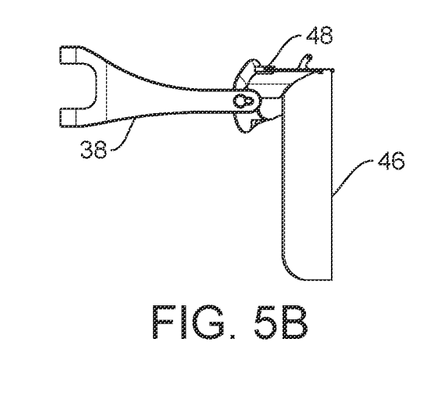
FIG. 5B is a right-side view of the face shield shown in FIG. 5A.
Figure 5C:
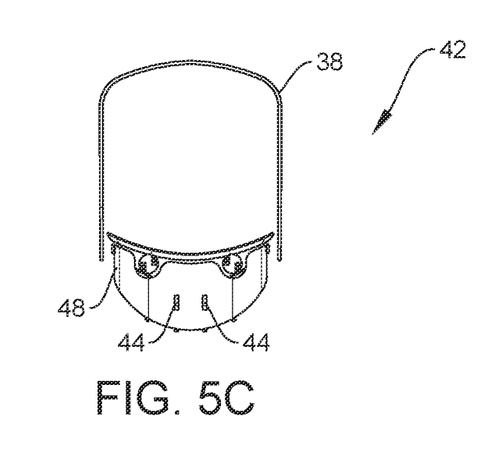
FIG. 5C is a top view of the face shield.
Figure 5D:
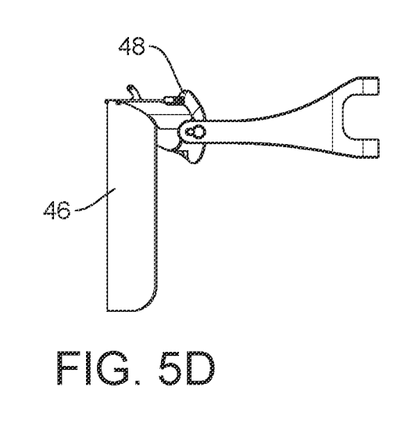
FIG. 5D is a left side view of the face shield.
Figure 5E:
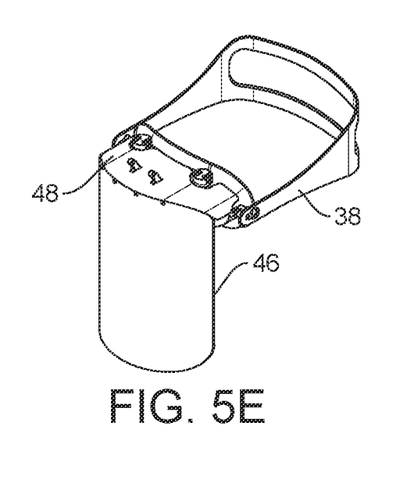
FIG. 5E is a top left perspective view of a face shield removably attached to the protective eyewear of the invention.
Figure 6A:
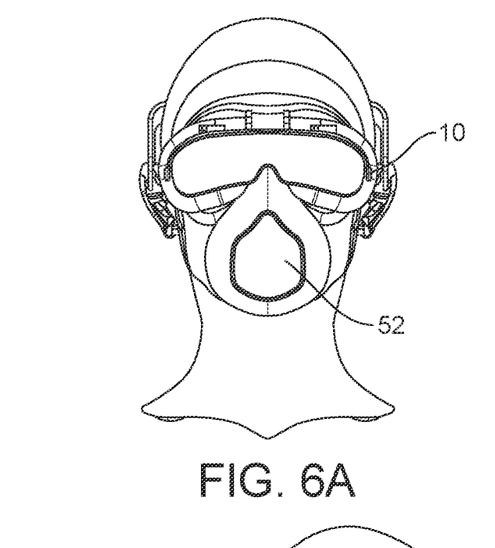
FIG. 6A is a front view of the face mask and protective eyewear of the invention as worn by a user.
Figure 6B:
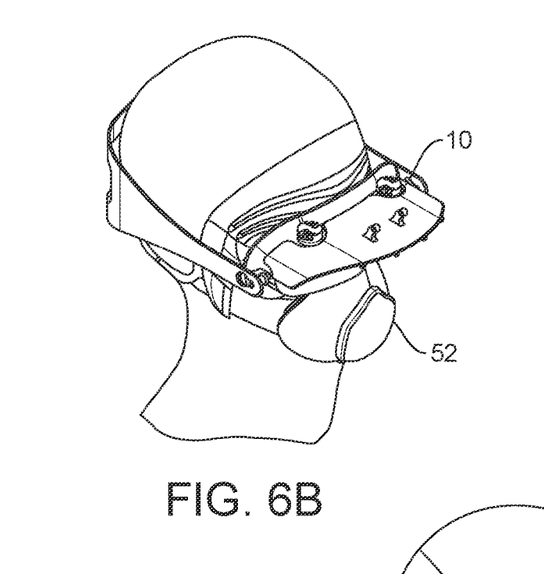
FIG. 6B is a right-side perspective view of the face mask and protective eyewear of the invention.
Figure 6C:
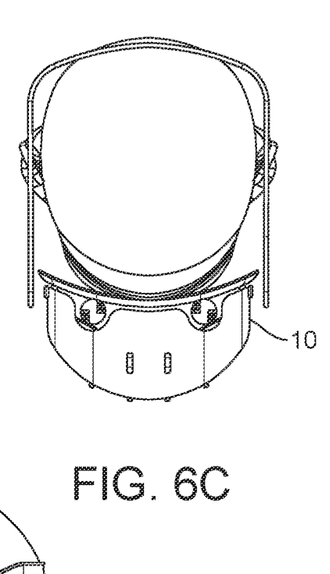
FIG. 6C is a top front view of the face mask and the protective eyewear of the invention.
Figure 6D:
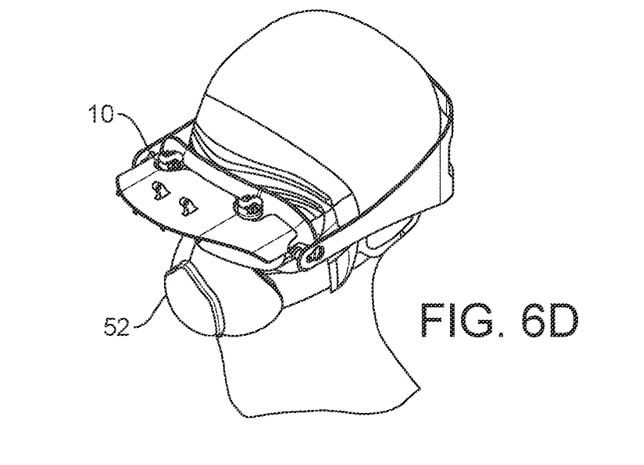
FIG. 6D is a left side perspective view of the face mask and protective eyewear of the invention.
Figure 6E:
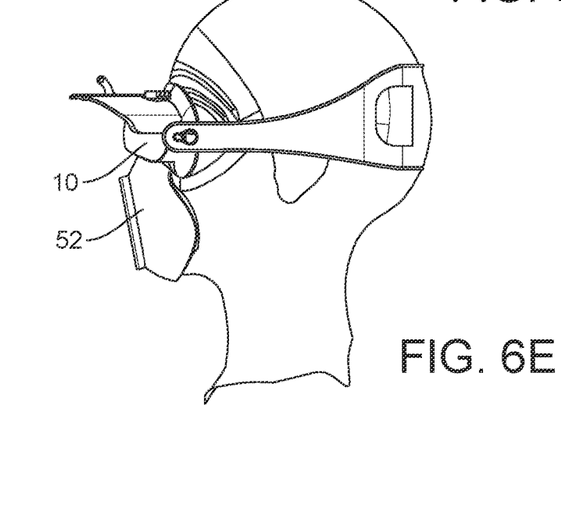
FIG. 6E is a left side view of the face mask and protective eyewear of the invention.

In another embodiment, the protective eyewear comprises a face seal 36, shown in FIG. 4A, that further comprises a bridge portion 56 that is configured to receive an accessory such as a face mask as well as allows the entire arrangement to sit snugly along the bridge of the nose of the user. FIG. 4B is a side view of the face seal 36 fitted into the lower frame 12 and upper frame 32 along with the lens 18 that fits in an airtight manner into a pair of slits 34 as an exemplary embodiment in a typical use case scenario. In FIG. 4B, the filter assembly receptacle 20 is also shown. The face seal 36 includes voids in the front occupied by lens 18 to allow visibility for the user.

Returning to FIG. 2, the protective eyewear 10 further includes a strap 38 that connects the side portions. The strap is made of an elastic material that enables the protective eyewear to be worn on the face of the user by looping around the back of the head of the user in a snug manner. The strap can have many shapes, wherein one exemplary embodiment shown herein. The strap may be configured to be removably fitted to the protective eyewear of the invention, for example, a snap-fit lock on the side of the protective eyewear that can be removed with ease, and attached whenever necessary by the user.

An accessory receiving extension 40 is made available as part of the protective eyewear 10 of the invention. The accessory receiving extension 40 includes suitable attachment means such as clips, snap locks, magnetized locks, and the like. In this manner, any other accessory, and in particular other personal protective equipment ("PPE"), can be attached to the protective eyewear of the invention. Exemplary attachments include face shields, flashlights, helmets, face masks, and the like. Such accessories would provide additional security such as splash protection or comfort such as extra visibility. In this manner, the user has the option to combine devices to secure onto the user's head, eliminating crossovers from multiple independent head straps from multiple PPE accessories which may pose problems with respect to proper fit and comfort issue.

The accessory receiving extension ensures a proper adjustable or fixed angle of the accessories onto the protective eyewear. In an exemplary embodiment, a light fixture attachment and a snap fitting for face shield can be attached to protective eyewear of the invention using the accessory receiving extension. A longer screw can be used to hold a light fixture holder that screws onto the frame which is held in place with fixed or adjustable angles. The attachment holds the additional PPE and/or device utilizing one head strap. Such adapter connections make it possible to use multiple PPE accessories for proper protection by eliminating clusters to provide better fit and comfort.

The protective eyewear 10 of the invention is advantageously built such that one or more of the components lower frame, upper frame, filter assembly, face seal and the accessory receiving extension are removably attached to the other components. Further, as noted herein, the filter assembly is configured such that at least one filter can be removed for cleaning or replacing.

FIGS. 5A through 5E illustrate one exemplary embodiment featuring a face shield 42 useful in the invention that can be attached to the accessory receiving extension 40 of the protective eyewear 10. In this case, the face shield is fitted using a snap fit attachment means 44 located on top of the accessory receiving extension. Other alternate arrangements such as, but not limited to, clasps on the side of the accessory receiving extension, interlocking fibers and so on, can be utilized to achieve the same purpose, and are envisioned to be within the scope of the invention.

Thus, in another aspect, the invention provides a face shield 42 that can be detachably attached to the protective eyewear 10 of the invention. The face shield includes a front portion 46 that is made of a transparent material and is generally curved to provide adequate protection for the face from contaminants. The face shield also includes a head portion 48 that is received by and integrates with the accessory receiving extension 40 of protective eyewear 10 as shown in FIG. 2. A strap or an adjustable loop 38 emanating from the sides of frame 12 as also shown in FIG. 2 secures the face shield protective eyewear assembly to the user's head. In this manner, the face shield is held in place on the forehead of the user and extends forward to protect the face. As already noted herein, the accessory receiving extension 40 of the invention also includes an attachment means 44 that allows head portion 48 of face shield 46 to be removably attached to the protective eyewear of the invention as described herein.

In some embodiments, the face shield is configured to swivel up and down. This may be enabled by holding the two ends of face shield with tensioning screws that inserts into visor and held in place with a nut. This allows the user to adjust tension and create a secure fastening point and desired angle on face shield. The face shield angle may be critical at times depending on the job task or other manufacture respirator mask. The face shield position can rotate from perpendicular to parallel standing point.

The face shield of the invention provides protection against pathogens contained in liquid droplets, and works together with the protective eyewear of the invention to provide strong protection against liquid droplets, airborne pathogens, aerosols, and generally airborne contaminants of a certain size, while allowing filtered air and oxygen to permeate through the filter. In the absence of a filter, the face shield in conjunction with the protective eyewear will still provide sufficient protection from liquid and particles.

The face shield and the protective eyewear of the invention are also designed to work together with other protective equipment such as face masks or accessories such as flashlights. One of the unique aspects of the invention lies in the ability of the protective equipment described herein to work together with other complementary protective equipment, being secured to the head with a single head strap, without compromising any of the PPEs' individual functions.

FIGS. 6A through 6E show yet another exemplary embodiment featuring a face mask 52 that is attached to the lower part of frame 12 of protective eyewear 10. Face mask 52 can alternatively be secured to the accessory receiving extension 40 of the protective eyewear 10.

The face mask is shaped such that it has a top portion that tapers to fit along the bridge of the nose of the user. Alternately, the nose bridge portion of the bottom frame 14 of the protective eyewear 10 of the invention is designed to be wide enough to receive the face mask. In this exemplary embodiment, the face mask may be configured such that a portion of it is allowed to go under the protective eyewear extending towards the lower part of the accessory receiving extension. Alternately, that portion may be configured to run over the protective eyewear in such a manner that it doesn't affect the viewing portion of the protective eyewear to be locked into place by the accessory receiving extension. In a further embodiment, a portion of the face mask may simply be allowed to go under the protective eyewear and the protective eyewear is configured to be held in place by virtue of tightening it against the face of the user through the use of the strap.

According to an exemplary embodiment, face mask 52 is secured to the user through loops attached to the face mask (not shown) that removably attach to knob 60 shown in FIG. 3B. Other means of removeably attaching face mask 52 to the frame 12 or the accessory attachment extension 40 of protective eyewear 10 are also envisioned. Alternatively, the face mask portion may be provided with its own strap to hold it tight against the face to provide a good seal against unventilated air.

SUMMARY AND SCOPE

Thus, the protective eyewear of the invention represents a significant advantage over existing protective eyewear in that the wider nose bridge accommodates proper fitment with a face mask and thus does not interfere or overlap with the eye protection. The protective eyewear also blocks hot air rising into eye space that causes fogging from masks not properly fitted and exhausting air from mask edges.

In another aspect, the invention provides a protective eyewear frame that comprises the lower frame and the upper frame. The lower and upper frames are configured to snugly fit into each other through suitable means such that it forms an air tight seal as described herein. The lower frame is further configured to be tapered along an inside portion such that it snugly fits against a bridge of a nose of the user. It will also be understood by one skilled in the art that the protective eyewear frame of the invention may include a mask skirt as described herein, wherein the mask skirt will comprise the tapered portion that allows it to fit snugly along the bridge of the nose. In this manner, suitable accessories such as a face mask can be used to synergistically protect the user against airborne pathogens contained in liquid droplets, aerosols, and generally airborne contaminants of a certain size, while allowing filtered air and oxygen to permeate through the filter.

While only certain features of the invention have been illustrated and described herein, many modifications and changes will occur to those skilled in the art. It is, therefore, to be understood that the appended claims are intended to cover all such modifications and changes as fall within the true spirit of the invention.

We claim:

1. A protective eyewear comprising:
   a frame having a front portion and side portions;
   lenses secured within said frame front portion;
   a strap detachably secured to and looping between said frame side portions;
   at least one filter assembly receptacle formed within said frame;
   at least one filter assembly removably secured within said filter assembly receptacle, said filter assembly comprising:
   (a) a housing;
   (b) at least one filter capable of filtering air of small particles;
   (c) a pressure lock mechanism for removably securing said housing within said filter assembly receptacle; and
   (d) a seal positioned between said housing and assembly receptacle;
   wherein said pressure lock mechanism with seal, when engaged with said assembly receptacle, form an air tight seal between said filter assembly and said frame;
   and wherein the filter assembly with filter is configured to allow ambient air to circulate into and out of said eyewear while at the same time blocking the entry of small particles.

2. The protective eyewear of claim 1, wherein said filter assembly is capable of blocking particles as small as 0.1 microns.

3. The protective eyewear of claim 1, wherein said seal is selected from a group consisting of an elastomeric seal in the form of an O-ring and a gasket in the form of an O-ring.

4. The protective eyewear of claim 1, wherein said pressure lock mechanism is a snap-fit lock.

5. The protective eyewear of claim 1, wherein said frame said frame comprising an upper frame and a lower frame, said lower frame comprising a bottom portion made from a rigid material and further comprising a flexible face seal configured to hold said lenses while forming an airtight seal between the eyewear and a face of a user, and wherein said filter assembly is formed within said lower frame.

6. The protective eyewear of claim 5, wherein said rigid said rigid material is made of polycarbonate and said flexible face seal is made of elastomeric material.

7. The protective eyewear of claim 1 wherein said frame also has a top portion and further comprises an accessory receiving extension secured to and extending forward from said frame top portion configured to removably receive and attach one or more accessories.

8. The protective eyewear of claim 7, wherein said accessories comprise personal protection equipment.

9. The protective eyewear of claim 7, wherein said accessories are selected from at least one of face shield accessory, face mask accessory, flashlight, or combinations thereof.

10. The protective eyewear of claim 1, wherein said frame further comprises a lower portion configured to fit snugly along the bridge of a nose of a user while accommodating a face mask worn concurrently with the eyewear.

11. A protective eyewear comprising:
a frame having a top portion, a front portion and side portions;
a strap detachably secured to and looping between said frame side portions;
lenses secured within the frame front portion;
an accessory receiving extension removably secured to and extending forward out from said frame top portion, said extension configured to removably receive, attach and secure, separately one or more accessories while holding said accessories a distance out from said frame and said lenses;
at least one filter assembly receptacle formed within said frame;
at least one filter assembly removably secured within said filter assembly receptacle, said filter assembly comprising:
(a) a housing;
(b) at least one filter capable of filtering air of small particles;
(c) a pressure lock mechanism for removably securing said housing within said filter assembly receptacle; and
(d) a seal positioned between said housing and assembly receptacle;
wherein said pressure lock mechanism with seal, when engaged with said assembly receptacle, form an air tight seal between said filter assembly and said frame;
and wherein the filter assembly with filter is configured to allow ambient air to circulate into and out of said eyewear while at the same time blocking the entry of small particles.

12. The protective eyewear of claim 11, wherein said filter assembly is capable of blocking particles as small as 0.1 microns.

13. The protective eyewear of claim 11, wherein said seal is selected from a group consisting of an elastomeric seal in the form of an O-ring and a gasket in the form of an O-ring.

14. The protective eyewear of claim 11, wherein said pressure lock mechanism is a snap-fit lock.

15. The protective eyewear of claim 11, wherein said frame comprising an upper frame and a lower frame, said lower frame comprising a bottom portion made from a rigid material and further comprising a flexible face seal configured to hold said lenses while forming an airtight seal between the eyewear and a face of a user, and wherein said filter assembly is formed within said lower frame.

16. The protective eyewear of claim 15, wherein said rigid said rigid material is made of polycarbonate and said flexible face seal is made of elastomeric material.

\* \* \* \* \*